United States Patent [19]

Yoshihara et al.

[11] Patent Number: 5,616,552
[45] Date of Patent: Apr. 1, 1997

[54] DETERGENT COMPOSITION COMPRISING N-ACYLTHREONINE SALT

[75] Inventors: Hideki Yoshihara, Kawasaki; Yoshihiro Kobayashi, Tokyo; Yasunobu Noguchi; Manabu Kitazawa, both of Kawasaki, all of Japan

[73] Assignee: Ajinomoto Co., Inc., Tokyo, Japan

[21] Appl. No.: 490,716

[22] Filed: Jun. 15, 1995

[30] Foreign Application Priority Data

Jun. 15, 1994 [JP] Japan .................................. 6-132849

[51] Int. Cl.$^6$ .......................... C11D 1/10; C11D 17/02; C11D 3/33
[52] U.S. Cl. .................. 510/490; 510/135; 510/137; 510/433; 510/437
[58] Field of Search .................. 510/490, 135, 510/137, 433, 437

[56] References Cited

U.S. PATENT DOCUMENTS

| | | | |
|---|---|---|---|
| 3,663,455 | 3/1972 | Yoshida et al. | 252/546 |
| 4,273,684 | 6/1981 | Nagashima et al. | 252/544 |
| 5,098,608 | 3/1992 | Miyazawa et al. | 510/490 |
| 5,326,493 | 7/1994 | Takahata et al. | 510/490 |
| 5,417,875 | 5/1995 | Nozaki | 510/490 |

OTHER PUBLICATIONS

Chemical Abstract:: 91–289353/40 90. 03. 29.
Chemical Abstract: 80–59568C/34 80. 07. 09.
Chemical Abstract: 82–65182E/31 82. 07. 10.

*Primary Examiner*—Paul Lieberman
*Assistant Examiner*—Necholus Ogden
*Attorney, Agent, or Firm*—Oblon, Spivak, McClelland, Maier & Neustadt, P.C.

[57] ABSTRACT

The present invention provides a novel detergent composition containing an N-acylthreonine salt which exhibits little irritation to the skin and hair as well as an improved foam maintenance, foam quality and feel upon use.

A detergent composition containing (A) N-acylthreonine salt in which the acyl group is a fatty acid residue having 8–22 carbon atoms and (B) higher fatty acid salt having 8–22 carbon atoms and also a detergent composition as such which further contains another surface-active agent.

21 Claims, No Drawings

DETERGENT COMPOSITION COMPRISING N-ACYLTHREONINE SALT

BACKGROUND OF THE INVENTION

1. Field of the Invention

The present invention relates to a detergent composition containing an N-acylthreonine salt and a higher fatty acid salt and, optionally, another surface-active agent. The detergent composition of the present invention exhibits little irritation and is safe. The detergent composition has improved foam maintenance, foam quality and feel upon use compared with other conventional detergent compositions.

2. Discussion of the Background

Conventional detergent compositions such as shampoo, face soap, kitchen detergent, etc. contain anionic surface-active agents such as higher fatty acid salts, polyoxyethylene alkyl ether sulfates, alkyl benzenesulfonates and the like. However, although the detergents mainly comprising such anionic surface-active agents exhibit excellent detergency, the feel upon actual use such as a creaking feel during rinsing and a stretching feel after use are not so satisfactory and, in addition, there is a disadvantage in that it exhibits much irritation to the skin and causes damage to the hair.

Surface-active agents which have been used and exhibit little irritation to the skin and hair and have an excellent detergency include N-acylamino acid salts, among them, N-acylglutamates (cf. "Functional Cosmetic Products" published by CMC, page 275, 1990), N-acyl sarcosine salts, N-acyl-N-methyl-β-alanine salts, N-acylmethyltaurine salts.

Other N-acylamino acid salts have also been studied and several N-acylamino acids have been synthesized from natural amino acids and synthesizable amino acids and investigated. There have been many reports on the investigations of N-acyl derivatives of natural amino acids.

It has been recently reported that the scum which is formed by N-acylglycine salts, N-acyl-β-alanine salts, etc. with calcium in tap water has been found to exhibit a good feel (cf. U.S. Pat. No. 5,185,113). However, with respect to the foaming properties of the N-acylamino acid salts in this report, they are not sufficient in terms of foam maintenance, creaminess, foaming ability and they also exhibit sliminess.

There have been rare cases in which N-(long-chain acyl) threonine (which is a kind of oxyamino acids) is used in detergent compositions. Examined Japanese Patent Publication Sho-39/029444 provides a detergent composition which does not chap the skin wherein 1–50% by weight of the above-mentioned substance is added to and compounded with a synthetic detergent of a mineral oil type or an alcohol type. However, no composition which has a satisfying feel upon use such as foam quality and finish after washing has been obtained. In the Japanese Laid-Open Patent Publication Sho-55/090594, there is a disclosure on a detergent composition containing N-acylated mixed amino acid salts and there is a description that the N-acyloxy amino acid salts exhibit a protective action to the skin and hair. However, although the resulting detergent composition is excellent in terms of the foaming and the creaking feel during rinsing, it has insufficient foam quality and finish after washing. Further, when the acylthreonine salt is used solely, there are similar problems as above and, moreover, there is another problem in that it cannot maintain a good foam.

SUMMARY OF THE INVENTION

Accordingly, one object of this invention is to provide a novel detergent composition with excellent detergency and with improved foam maintenance, foam quality and feel upon use.

The present inventors have found that, when an N-acylthreonine salt is jointly used with a higher fatty acid salt or when another surface-active agent is used in addition to these, the above-mentioned object can be achieved.

DESCRIPTION OF THE PREFERRED EMBODIMENTS

Thus, the present invention relates to a detergent composition which comprises (A) an N-acylthreonine salt in which the acyl group is a fatty acid residue having 8–22 carbon atoms and (B) a higher fatty acid salt having 8–22 carbon atoms.

The acyl group of the N-acylthreonine salt is an acyl residue of saturated or unsaturated fatty acid having 8–22 carbon atoms. Suitable acyl groups include acyl residues of fatty acids of a single composition such as lauric acid, myristic acid, palmitic acid, stearic acid and oleic acid and also acyl residues of the mixed fatty acids obtained from nature such as coconut oil fatty acids, tallow fatty acids, hydrogenated tallow fatty acids, castor oil fatty acids, olive oil fatty acids and palm oil fatty acids as well as those of the fatty acids (including branched ones) obtained through synthesis.

Preferred examples of the N-acylthreonine salts are the salts of N-lauroylthreonine, N-myristoylthreonine, N-palmitoylthreonine, N-stearoylthreonine, N-oleoylthreonine, N-cocoylthreonine and an acylthreonine derived from N-hydrogenated tallow fatty acids. Those N-acylthreonine salts may be optically active or racemic.

The basic component of the N-acylthreonine salts suitably are alkali metals such as sodium and potassium; alkali earth metals such as magnesium and calcium; organic amines such as monoethanolamine, diethanolamine, triethanolamine, 2-amino-2-methyl-1-propanol and 2-amino-2-methyl-1,3-propanediol; basic amino acids such as lysine, ornithine and arginine; and ammonia. Two or more of those basic components may be used jointly.

The higher fatty acid salt of the component (B) of the detergent composition of the present invention is a salt with a linear or branched and saturated or unsaturated fatty acid having 8–22 carbon atoms. Preferred examples are the salts with lauric acid, myristic acid, palmitic acid, stearic acid, coconut oil fatty acid, hydrogenated tallow fatty acid, behenic acid and oleic acid. Examples of the basic component for such a salt are alkali metals such as sodium and potassium; alkali earth metals such as magnesium and calcium; organic amines such as monoethanolamine, diethanolamine, triethanolamine, 2-amino-2-methyl-1-propanol and 2-amino-2-methyl-1,3-propanediol; basic amino acids such as lysine, ornithine and arginine; and ammonia. Those basic components may be used either solely or jointly by combining two or more of them.

The combining ratio of the components (A) to (B) in the detergent composition of the present invention are suitably selected within a range from 0.5:99.5 to 99.5:0.5 by weight depending upon the property of the final product. When the amount of the component (B) is less than 0.5, the foam amount is sufficient but the foam maintenance is poor and the foam quality is rough and, in addition, there is a problem in the finish after washing resulting in some sliminess. On the other hand, when the compounding ratio of the component (A) is less than 0.5, the foam maintenance is satisfactory but there are problems in term of the feel upon use, that a creaky feel results upon rinsing and, moreover, that there is another problem of irritation to the hair and skin.

The total compounding amount of (A) and (B) in the detergent composition of the present invention may vary depending upon the form of the detergent composition but, preferably, it is from 5 to 95% by weight.

The present invention further provides a detergent composition in which foaming ability and foam maintenance are excellent, the foams are fine and creamy, the creaking feel upon rinsing is reduced and the finish after washing is fresh whereby the feel is improved by compounding a suitable amount of a third surface-active agent with components (A) and (B).

Examples of such a surface-active agent are anionic surface-active agents of the carboxylate type (excluding the components (A) and (B)), sulfonate type and sulfate type; cationic surface-active agents of an aliphatic amine quaternary ammonium salt type, an aromatic quaternary ammonium salt type and a mono(long-chain acyl) basic amino acid lower alkyl ester salt type; nonionic surface-active agents of an alkylglycoside type and an aliphatic alkanolamide type; and amphoteric surface-active agents of a betaine type and an imidazoline type.

As hereinafter, various surface-active agents which are used as the third component for the detergent composition of the present invention will be described in detail.

First, anionic surface-active agents will be described.

Examples of the surface-active agent of the carboxylate type are of the N-acylaminocarboxylate type and an ether carboxylate type.

In the anionic surface-active agent of an N-acylamino carboxylate type, the acyl group is an acyl residue of saturated or unsaturated fatty acid having 8–22 carbon atoms. Examples of it are acyl residues of fatty acids of a single composition such as lauric acid, myristic acid, palmitic acid, stearic acid and oleic acid and also are acyl residues of the mixed fatty acids obtained from nature such as coconut oil fatty acids, tallow fatty acids, hydrogenated tallow fatty acids, castor oil fatty acids, olive oil fatty acids and palm oil fatty acids as well as of the fatty acids (including branched ones) obtained through synthesis. Examples of the aminocarboxylic acid binding therewith are acidic amino acids such as glutamic acid, aspartic acid, cysteic acid and homocysteic acid; neutral amino acids such as glycine, alanine, valine, leucine, isoleucine, phenylalanine, tryptophane, sarcosine, beta-alanine, gamma-aminobutyric acid, epsilon-aminocaproic acid, serine, homoserine, tyrosine, proline, hydroxyproline, cystine, cysteine and methionine; and basic amino acids such as lysine, ornithine and arginine. With respect to those acylaminocarboxylic acids, any optical isomer or racemic compound may be used.

Examples of the surface-active agent of an ether carboxylate type are polyoxyethylene alkyl ether acetates and polyglyceryl alkyl ether acetates and more specific examples are polyoxyethylene lauryl ether acetate and polyoxyethylene tridecyl ether acetate.

Examples of the surface-active agents of a sulfonate type are anionic surface-active agents of a sulfosuccinate type and anionic surface-active agents of an organic sulfonate of monobasic acid type such as those of an alkylsulfonate type, an ester sulfonate type and an N-acylsulfonate type.

Examples of the above-mentioned anionic surface-active agent of a sulfosuccinate type are sulfosuccinates of higher alcohol represented by the following general formula (1) or (2) or ethoxylate thereof or sulfosuccinates derived from higher fatty acid amides or salts thereof.

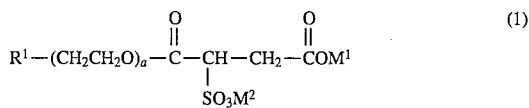

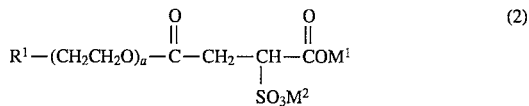

In the above formulae, $R^1$ is $R^2$—O— or $R^3$—CONH— (in which $R^2$ is a linear or branched alkyl or alkenyl having 8–22 carbon atoms and $R^3$ is a linear or branched alkyl or alkenyl having 7–21 carbon toms); $M^1$ and $M^2$ each is a hydrogen atom or a cation selected from alkali metal, alkaline earth metal, ammonium and organic ammonium independently; and a is an integer of 0–20.

The specific examples are undecylenoylamide ethylsulfosuccinate, polyoxyethylene lauroylethanolamide sulfosuccinate salt, lauryl sulfosuccinate salt, polyoxyethylene lauryl sulfosuccinate salt and oleic acid amide sulfosuccinate.

Examples of the above-mentioned anionic surface-active agent of an organic sulfonate of monobasic acid type are $C_{8-22}$ linear or branched alkyl or alkenyl sufonates, alkyl benzenesulfonates having a linear or branched alkyl group of 10–16 carbon atoms and N-acylsulfonates or O-acylsulfonates in which the acyl group is a linear or branched and saturated or unsaturated fatty acid residue having 8–22 carbon atoms.

Specific examples are alkanesulfonates, α-olefinsulfonates, alkyl benzenesulfonates, acyl methyltaurine salts, isethionic acid fatty acid ester salts and α-sulfonated fatty acid ester salts.

Examples of the anionic surface-active agent of a sulfate type are the surface-active agents such as alkyl sulfate salts and ether sulfate salts.

The above-mentioned anionic surface-active agent of an alkyl sulfate salt type is a salt of an ester of a $C_{8-22}$ linear or branched and saturated or unsaturated higher alcohol with sulfuric acid and examples of it are lauryl sulfate salts, myristyl sulfate salts and oleyl sulfate salts.

The above-mentioned anionic surface-active agent of an ether sulfate type is an alkylene oxide adduct of the above-mentioned alkyl sulfate salt and its examples are polyoxyethylene lauryl ether sulfates, polyoxyethylene myristyl ether sulfates and polyoxyethylene oleyl ether sulfates.

Examples of the basic component of these various anionic surface-active agents are alkali metals such as sodium and potassium; alkaline earth metals such as magnesium and calcium; organic amines such as monoethanolamine, diethanolamine, triethanolamine, 2-amino-2-methyl-1-propanol and 2-amino-2-methyl-1,3-propanediol; basic amino acids such as lysine, ornithine and arginine; and ammonia. Those basic components may be used either solely or jointly by combining two or more of them.

The compounding ratio of the above-mentioned various anionic surface-active agents may be selected depending upon the property of the final product, but usually the agents are compounded at a ratio within a range of from 1/15 to 15/1 to the total amount (by weight) of components (A) and (B).

Below, described is the cationic surface-active agent which is used as the third component of the detergent composition of the present invention.

The aliphatic amine quaternary ammonium salt is, for example, a linear mono or dialkyl quaternary ammonium salt represented by the following general formula (3).

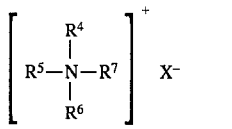

In the above formula, one or two of $R^4$–$R^7$ are long-chain alkyl having 8–24 carbon atoms while others are alkyl or hydroxyalkyl having 1–3 carbon atoms; and X is a halogen atom or an alkyl sulfate group having 1 or 2 carbon atoms.

Preferred examples of such an ammonium salt are mono-(long-chain alkyl) quaternary ammonium salts such as lauryl trimethylammonium chloride, myristyl trimethylammonium chloride, palmityl trimethylammonium chloride, stearyl trimethylammonium chloride, oleyl trimethylammonium chloride, cetyl trimethylammonium chloride, cetyl trimethylammonium methylsulfate, eicosyl trimetylammonium chloride and behenyl trimethylammonium chloride; and di(long-chain alkyl) quaternary ammonium salts such as dipalmityl dimethylammonium chloride, distearyl dimethylammonium chloride, di(hydrogenated tallow alkyl) dimethylammonium bromide and di(hydrogenated tallow alkyl) dimethylammonium methylsulfate. They may be used either solely or jointly by combining two or more of them.

The aromatic quaternary ammonium salt is, for example, a benzalconium salt represented by the following general formula (4).

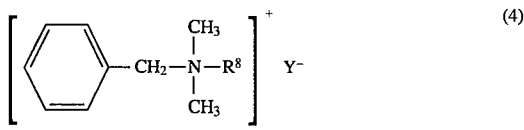

In the above formula, $R^8$ is an alkyl having 8–24 carbon atoms; and Y is a halogen atom or an alkyl sulfate group having 1 or 2 carbon atoms.

Preferred examples of the benzalconium salt are lauryl dimethylbenzylammonium chloride and stearyl dimethylbenzylammonium chloride. They may be used either solely or jointly by combining two or more of them.

In the cationic surface-active agent of a mono(long-chain acyl) basic amino acid lower alkyl ester salt type, the acyl group is an acyl residue of a fatty acid having 8–22 carbon atoms and examples of it are lauroyl, cocoyl, myristoyl, palmitoyl, stearoyl and oleyl. Examples of the basic amino acid binding therewith are natural amino acids such as lysine, ornithine and arginine and any optically active or racemic substances may be used. Examples of the salt for the mono(long-chain acyl) basic amino acid lower alkyl ester salt are inorganic salts such as hydrochloride and sulfate; and organic salts such as acetate, tartrate, citrate, p-toluenesulfonate, fatty acid salts, acidic amino acid salts and pyroglutamate. Suitable lower alkyl ester components are methyl ester, ethyl ester, propyl ester, butyl ester, pentyl ester, hexyl ester, heptyl ester and octyl ester.

They may be used either solely or jointly by combining two or more of them.

The compounding amount of the above-mentioned various cationic surface-active agents may suitably selected depending upon the property of the final product but, usually, the amount in the detergent composition is from 0.01 to 5.0% by weight.

In the following, an illustration will be made for the nonionic surface-active agent used as the third component for the detergent composition of the present invention.

An example of the alkyl glycoside used is that which is represented by the following general formula (5).

In the above formula, $R^9$ is a linear or branched alkyl or alkenyl having 8–18 carbon atoms; $R^{10}$ is an alkylene group having 2–4 carbon atoms; G is a residue derived from a reducing sugar having 5–6 carbon atoms; the average value of b is 0–5; and the average value of c is 1–10.

When the average value of c is 1 or more in the above general formula (5) or, in other words, when a sugar chain of di- or higher saccharide is used as a hydrophilic group, the binding mode of the sugar may be a 1–2, 1–3, 1–4 or 1–6 bond or, moreover, α- or β-pyyranoside or furanoside bond or any mixture being in the mixed mode thereof. With respect to the value of b, it is preferably 0–2 in terms of water solubility and crystallinity while the preferred value of c is about 1–3 in terms of foam-increasing effect.

$R^9$ is a linear or branched alkyl, alkenyl or alkylphenyl having 8–18 carbon atoms but, the preferred carbon atom numbers from a standpoint of solubility, foaming ability and detergency are 10–14. $R^{10}$ is an alkylene group having 2–4 carbon atoms but the preferred value from the standpoint of water solubility is 2–3. The structure of G is decided by the material which is monosaccharide or di- or higher saccharide and examples of the material for G in the case of monosaccharide are glucose, galactose, xylose, mannose, lyxose, arabinose and a mixture thereof while those in the case of di- or higher saccharide are maltose, xylobiose, isomaltose, cellobiose, gentiobiose, lactose, sucrose, negerose, turanose, raffinose, gentianose, melezitose and a mixture thereof. Among those, preferred materials are glucose and fructose for monosaccharide and are maltose and sucrose for di- or higher saccharide due to their availability and low cost.

Those alkylglycosides may be used either solely or jointly by combining two or more of them.

An example of the aliphatic alkanolamide is that which is represented by he following general formula (6).

In the above formula, $R^{11}$ is an alkyl group having 8–20 carbon atoms; and $R^{12}$ and $R^{13}$ are same or different and each of them is a hydrogen atom, a hydroxyalkyl group having 1–3 carbon atoms or a $-(C_2H_4O)_dH$ group (where d is an integer of 2–4).

In the above formula, the preferred carbon numbers of the alkyl for $R^{11}$ are 12–18 and a preferred combinations for $R^{12}$ and $R^{13}$ are that both of them are hydroxyalkyl (particularly hydroxyethyl) and that one of them is a hydoxyalkyl (particularly hydroxyethyl) while another is a hydrogen atom.

Specific examples of the aliphatic alkanolamide are coconut oil fatty acid monoethanolamide, coconut oil fatty acid diethanolamide, lauric acid monoethanolamide and lauric acid diethanolamide. They may be used either solely or jointly by combining two or more of them.

The compounding ratio of the above nonionic surface-active agent may be suitably selected depending upon the property of the final product, but usually the ratio of the alkylglycoside represented by the general formula (5) and that of the aliphatic alkanolamide represented by the general formula (6) to the total amount of components (A) and (B) are within ranges of 1/15–15/1 and 1/100–1/2, respectively.

The illustration will now be made for the amphoteric surface-active agent used as the third component of the detergent composition of the present invention.

Examples of the amphoteric surface-active agent of the betaine type are surface-active agent of the carbobetaine type, that of an amidobetaine type, that of a sulfobetaine type, that of a hydroxysulfobetaine type, that of an amidosulfobetaine type and that of a phosphobetaine type.

In other words, the surface-active agent of a betaine type as such has, for example, alkyl, alkenyl or acyl having 8–24 carbon atoms. More specific examples are coconut oil alkyldimethylaminoacetic acid betaine, coconut oil fatty acid amide propyldimethylaminoacetic acid betaine, stearyl dihydroxyethylaminoacetic acid betaine, lauryl hydroxysulfobetaine, lauryl sulfobetaine and lauryl phosphobetaine. Those amphoteric surface-active agents of a betaine type may be used either solely, or jointly by combining two or more of them.

Examples of the amphoteric surface-active agent of an imidazoline type are those having $C_{8-22}$ alkyl group such as 2-alkyl-N-carboxymethyl-N-hydroxyethylimidazolinium betaine, 2-alkyl-N-carboxyethyl-N-hydroxyethylimidazolinium betain and 2-alkyl-N-carboxymethyl-N-carboxymethyloxyethyl-imidazolinium betaine. They may also be used either solely, or jointly by combining two or more of them.

The mixing ratio of the above-mentioned various amphoteric surface-active agents may be selected depending upon the property of the final product and, usually, they are compounded within a range of from 1/15 to 15/1 to the total weight of the components (A) and (B).

The total compounding amount of the components (A) and (B) and the third component in the detergent composition of the present invention may vary depending upon the form of the detergent composition but, preferably, it is from 5 to 95% by weight of the detergent composition.

There is no particular limitation in terms of the form of the detergent in the detergent composition of the present invention and any of the forms of liquid, paste, gel, solid, powder, etc. may be adopted. The pH of such a detergent is 5–9 or, preferably, 6–8. In the case of the detergent composition of the present invention in which N-acrylthreonine salt is used, the foam property is not deteriorated, unlike the composition using other N-acyl neutral amino acid salt such as N-acylalanine salt or N-acylglycine salt, even if the pH is 7 or less and, therefore, a product with little irritation to the skin can be prepared. Other components which are common for use in detergent compositions may be added to the detergent composition of the present invention so far as they do not inhibit the effect of the present invention. Examples of such other common components for the detergent compositions are polyhydric alcohols such as diglycerol, octanediol, maltitol, diethylene glycol, polyethylene glycol, ethylene glycol, propylene glycol, dipropylene glycol, polypropylene glycol, isopropylene glycol, pentyaerythritol, glucose, trehalose, fructose, 1,3-butylene glycol, glycerol and sorbitol; moisturizing agents such as sodium DL-pyrrolidonecarboxylate and sodium lactate; emulsifiers such as glycerol monostearate, sorbitan monopalmitate, sorbitan monostearate, sorbitan monooleate, sorbitan monosesquioleate, sorbitan monolaurate, polyglycerol monostearate, polyoxyethylene cetyl ether, polyoxyethylene stearyl ether, polyoxyethylene sorbitan monolaurate, diglycerol monostearate, polyethylene glycol monostearate, polyethylene glycol monooleate, polyethylene glycol monolaurate, polyethylene glycol distearate, polyethylene glycol dioleate, polyethylene glycol dilaurate, polyoxyethylene oleyl ether, polyoxyethylene lauryl ether, polyoxyethylene nonylphenyl ether, polyoxyethylene octylphenyl ether, polyoxyethylene sorbitol bees wax, polyoxyethylene sorbitan monostearate, polyoxyethyene sorbitan monooleate, polyoxyethylene sorbitan monolaurate and ethylene glycol monostearate; triglycerides such as avocado oil, almond oil, olive oil, cacao butter, beef tallow, sesame oil, wheat germ oil, safflower oil, shea butter, turtle oil, tsubaki oil, persic oil, castor oil, grape oil, macademia nut oil, mink oil, egg yolk oil, wood wax, coconut oil, rose hip oil, soybean oil, cotton seed oil and hydrogenated oil; wax such as orange raffy oil, carnauba wax, candelilla wax, whale wax, jojoba oil, monta wax, bees wax and lanolin; hydrocarbons such as liquid paraffin, paraffin, vaseline, ceresin, microcrystalline wax, solid paraffin, squalane and olefin oligomers; higher alcohols such as lauryl alcohol, cetyl alcohol, cetostearyl alcohol, stearyl alcohol, oleyl alcohol, behenyl alcohol, lanolin alcohol, hydrogenated lanolin alcohol, hexyldecanol, octyldecanol, isostearyl alcohol, jojoba alcohol and decyltetradecanol; sterols such as cholesterol, dihydroxycholesterol and phytosterol; esters such as oleyl oleate, ethyl linolate, isopropyl myristate, isopropyl lanolate, hexyl laurate, myristyl myristate, cetyl myristate, isopropyl palmitate, stearyl stearate, octyldodecyl myristate, decyl oleate, octyldodecyl oleate, hexyldecyl dimethyloctanoate, cetyl isooctanoate, cetyl palmitate, glycerol trimyristate, glycerol tris(caprylcaprate), propylene glycol dioleate, glycerol triisostearate, glycerol triisooctanoate, cetyl lactate, myristyl lactate, diisostearyl malate, cholesteryl stearate, cholesteryl isostearate, cholesteryl 12-hydroxystearate, glyceryl pyroglutamate oleate, di(cholesteryl, behenyl or octyldodeyl alcohol) N-lauroyl-L-glutamate and triglycerol 2-ethylhexanoate; polymers such as methylcellulose, hydroxyethylcellulose, hydroxypropylcellulose, ethylcellulose, nitrocellulose, sodium carboxymethylcellulose, carboxyvinyl polymer, polyvinyl methyl ether, polyvinyl alcohol, crystalline cellulose, arabic gum, tragacanth gum, guar gum, locust bean gum, karaya gum, iris moss, queens seed, gelatin, shellac, rosin, casein, sodium alginate, ester gum, polyvinylpyrrolidone, sodium polyacrylate, polyamide resin, silicone oil, chitin, partially deacetylated chitin, hydrolyzed collagen, polyaspartic acid, sodium polyglutamate and xanthan gum; antiseptics/antifungals such as cresol derivatives and paraben derivatives; pharmaceuticals and effective materials such as antiinflammatory agents, crude drugs, vitamins, hair growth promoters, whitening agents, UV absorbers and hormones; cosmetic materials such as pH-adjusting agents, feel-improving agents, perfatty agents, inorganic salts, amino acids, pearling agents, viscosity-adjusting agents, perfumes, dyes, softeners and mitigating agents; chelating agents such as ethylenediaminetetraacetic acid, citric acid, maleic acid, succinic acid, ascorbic acid, cephalin, gluconic acid, saccharinic acid, hexametaphos-phoric acid, 1-hydroxyethane-1,1-diphosphonic acid, dihydoxyethylglycine and salts thereof; and animal and plant extracts such as placenta extract, licorice extract, hamamelis solution, sponge cucumber solution, elastin, aloe extract and chamomilla extract.

EXAMPLES

Having generally described this invention, a further understanding can be obtained by reference to certain specific examples which are provided herein for purposes of illustration only and are not intended to be limiting unless otherwise specified.

Preparation Example 1

(N-Acylthreonine Salt)

N-Lauroyl-L-threonine was synthesized by a method described in Examined Japanese Patent Publication Sho-51/

038681. The by-produced impurities were removed by means of a recrystallization and the resulting high-purity N-lauroyl-L-threonine was neutralized with potassium hydroxide or triethanolamine to give potassium salt of N-lauroyl-L-threonine or triethanolamine salt of N-lauroyl-L-threonine, respectively. They were used in the following examples.

(a) Comparative Examples 1–4 and Examples 1–6

(Evaluations on Maintaining Ability of Foams and on Creaminess and Organoleptic Evaluation)

Potassium salt of N-lauroyl-L-threonine (hereinafter, may be abbreviated as "lauroylthreonine K") and triethanolamine salt of N-lauroyl-L-threonine (hereinafter, may be abbreviated as "lauroylthreonine TEA") prepared in the Manufacturing Example 1 and potassium laurate (hereinafter, may be abbreviated as "K laurate") and triethanolamine laurate (hereinafter, may be abbreviated as "TEA laurate") were taken in various proportions (by weight) as shown in Table 3 which will be shown later and aqueous solutions in which the total concentration of the surface-active agents was 0.5% by weight were prepared using distilled water.

Each aqueous solution (50 g) was stirred with a mixer for domestic use (350 ml; manufactured by Iwatani Sangyo KK) and the volumes (ml) of the foams after allowing them to stand for one minute and ten minutes were measured whereby the foam amount and the foam maintenance (rate of maintaining the foams) were evaluated. With respect to the creaminess, the foams were placed on a slide glass immediately after foaming, covered with a covering glass and evaluated through observation under a microscope. The following Table 1 shows the evaluation standards for each of the evaluating items.

TABLE 1

(1) Bubble volume: bubble volume after 1 minute

⊚; ≧250 ml, o; 200–250 ml, Δ; 150–200 ml, ×; 150 ml>

(2) Retention of bubbles:

o; ≧85%, Δ; 80–85%, ×; 80%>

$$\text{retention (\%)} = \frac{\text{(bubble volume after 10 minutes)}}{\text{(bubble volume after 1 minute)}} \times 100$$

(3) Creaminess of bubbles:

⊚; very creay, o; creamy, Δ; usual, ×; not sufficient

Then the feel upon washing (feel or touch of the foams, creakiness and freshness) as a detergent for hair and body was evaluated in organoleptic evaluation by ten female and ten male panellers and the total evaluation was conducted as well. The organoleptic evaluation was carried out as follows. Thus, the surface-active agents were taken in the proportions as given in Table 3, made into aqueous solutions of 15% or 30% using distilled water and each of the aqueous solutions was subjected to the tests for washing hands and for washing hair. The evaluation standards for each of the evaluating items are given in the following Table 2. In the meanwhile, it was found that, with respect to the total evaluation, three points or less were insufficient for actual use while four points or more were satisfactory for actual use.

TABLE 2

(1) Touch of bubbles:
⊚; very good, O; good, Δ; usual, X; bad
(2) Jarring feeling (hands):
⊚; very smooth, O; smooth, Δ; usual, X; extremely jarring
(3) Jarring feeling (hair):
same manner for hands
(4) Refreshed feeling:
⊚; very refreshed, O; refreshed, Δ; usual, X; slimy
(5) Total evaluation:
⊚; 2 points, O; 1 point, Δ; 0 point, X; −1 point
Evaluated by the total point. The criteria are as follows:
5; ≧10 points, 4; 6–10 points, 3; 2–6 points,
2; −2–2 points, 1; −2 points >

The results of the evaluations are given in the following Table 3.

| | 1 | 2 | 3 | 4 | 1 | 2 | 3 | 4 | 5 | 6 |
|---|---|---|---|---|---|---|---|---|---|---|
| Potassium N-lauroylthreonate | 100 | | | | 15 | 50 | 85 | | | |
| Triethanolamine N-lauroylthreonate | | 100 | | | | | | 15 | 50 | 85 |
| Potassium laurate | | | 100 | | 85 | 50 | 15 | | | |
| Triethanolamine laurate | | | | 100 | | | | 85 | 50 | 15 |
| Bubble volume | ⊚ | ⊚ | ⊚ | ⊚ | ⊚ | ⊚ | ⊚ | ⊚ | ⊚ | ⊚ |
| Retention of bubbles | X | X | Δ | Δ | O | O | O | O | O | O |
| Creaminess of bubbles | X | X | O | O | ⊚ | ⊚ | O | ⊚ | ⊚ | O |
| Touch of bubbles | Δ | Δ | O | O | O | ⊚ | O | O | ⊚ | O |
| Jarring feeling (hands) | O | O | X | X | O | O | O | O | O | O |
| Jarring feeling (hair) | O | O | X | X | Δ | Δ | O | Δ | Δ | O |
| Refreshed feeling | Δ | Δ | ⊚ | ⊚ | ⊚ | O | O | ⊚ | O | O |
| Total evaluation | 3 | 3 | 3 | 3 | 4 | 4 | 4 | 4 | 4 | 4 |

It is clear from Table 3 that, although the sole use of N-acylthreonine salt is insufficient in terms of the foam maintenance and the creaminess of foams, addition of higher fatty acid salt to the N-acylthreonine salt results in an improved foam maintenance and creaminess of foams. Moreover, the touch of the foams, creakiness and freshness is improved through the synergistic action of both components.

(b) Comparative Examples 5–24 and Examples 7–79

N-Lauroylthreonine salt and higher fatty acid salt were used together with other surface-active agents as the third components, i.e. anionic, cationic, nonionic and amphoteric surface-active agents in the amounts as shown in Tables 4 to 10 and evaluations were made in the same manner as in the above-mentioned examples. The results of the evaluations are given in Tables 4 to 10 as well.

It is understood from the results of Tables 4–10 that the three-componential system wherein an N-lauroylthreonine salt, a higher fatty acid salt and another surface-active agent are compounded exhibits improved foam properties and feel upon use as compared with the two-componental system. In evaluations, the detergent compositions of the present invention gained four points or higher (of a total of five points) in all cases and thus are considered excellent for actual use.

|  | 5 | 6 | 7 | 8 | 9 | 10 | 11 | 12 | 13 | 14 | 15 |
|---|---|---|---|---|---|---|---|---|---|---|---|
| Triethanolamine N-lauroylthreonate | 15 | 15 |  |  |  |  |  |  | 70 | 75 |  |
| Potassium N-lauroylthreonate |  |  | 15 |  | 35 | 35 |  |  |  |  | 35 |
| Sodium laurate |  |  |  |  |  |  |  |  |  |  |  |
| Triethanolamine laurate |  |  |  |  |  |  |  |  |  |  |  |
| Triethanolamine N-cocoylglutamate | 85 |  |  |  |  |  |  |  |  |  |  |
| Triethanolamine N-lauroylsarconate |  | 85 |  |  |  |  |  |  |  |  |  |
| Sodium N-lauroyl-N-methyl-β-alanate |  |  | 85 |  |  |  |  |  |  |  |  |
| Sodium polyoxyethylene lauryl acetate |  |  |  | 100 |  |  |  |  |  |  |  |
| Sodium cocoylisethionate |  |  |  |  | 65 |  |  |  |  |  |  |
| Sodium lauroylmethytaurate |  |  |  |  |  | 65 |  |  |  |  |  |
| Disodium lauryl sulfosuccinate |  |  |  |  |  |  | 100 |  |  |  |  |
| Disodium lauryl polyoxyethylene sulfosuccinate |  |  |  |  |  |  |  | 100 |  |  |  |
| Triethanolamine lauryl sulfonate |  |  |  |  |  |  |  |  | 30 |  |  |
| Triethanolamine polyoxyethylene lauryl sulfonate |  |  |  |  |  |  |  |  |  | 25 |  |
| Sodium α-Olefin sulfonate (C12) |  |  |  |  |  |  |  |  |  |  | 65 |
| Bubble volume | Δ | O | ⊙ | O | O | O | O | Δ | ⊙ | O | Δ |
| Retention of bubbles | Δ | Δ | Δ | X | Δ | Δ | X | X | Δ | X | X |
| Creaminess of bubbles | Δ | Δ | Δ | Δ | X | Δ | X | X | X | X | X |
| Touch of bubbles | Δ | Δ | Δ | Δ | X | Δ | X | X | Δ | Δ | X |
| Jarring feeling (hands) | X | X | X | Δ | Δ | X | Δ | Δ | Δ | Δ | Δ |
| Jarring feeling (hair) | Δ | X | X | X | X | X | Δ | Δ | Δ | Δ | Δ |
| Refreshed feeling | X | X | X | Δ | Δ | X | Δ | X | X | X | Δ |
| Total evaluation | 2 | 2 | 2 | 2 | 2 | 2 | 2 | 1 | 2 | 2 | 1 |

|  | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|
| Triethanolamine N-lauroylthreonate | 10 | 10 | 80 | 35 | 10 | 10 | 80 | 35 |  |  |  |  | 10 | 10 | 80 | 35 |
| Potassium N-lauroylthreonate |  |  |  |  |  |  |  |  | 10 | 10 | 80 | 35 |  |  |  |  |
| Sodium laurate |  |  |  |  |  |  |  |  | 10 | 80 | 10 | 35 |  |  |  |  |
| Triethanolamine laurate | 10 | 80 | 10 | 35 | 10 | 80 | 10 | 35 |  |  |  |  | 10 | 80 | 10 | 35 |
| Triethanolamine N-cocoylglutamate | 80 | 10 | 10 | 30 |  |  |  |  |  |  |  |  |  |  |  |  |
| Triethanolamine N-lauroylsarconate |  |  |  |  | 80 | 10 | 10 | 30 |  |  |  |  |  |  |  |  |
| Sodium N-lauroyl-N-methyl-β-alanate |  |  |  |  |  |  |  |  | 80 | 10 | 10 | 30 |  |  |  |  |
| Sodium polyoxyethylene lauryl acetate |  |  |  |  |  |  |  |  |  |  |  |  | 80 | 10 | 10 | 30 |
| Sodium cocoylisethionate |  |  |  |  |  |  |  |  |  |  |  |  |  |  |  |  |
| Sflium lauroylmethytaurate |  |  |  |  |  |  |  |  |  |  |  |  |  |  |  |  |
| Disodium lauryl sulfosuccinate |  |  |  |  |  |  |  |  |  |  |  |  |  |  |  |  |
| Disodium lauryl polyoxyethylene sulfosuccinate |  |  |  |  |  |  |  |  |  |  |  |  |  |  |  |  |
| Triethanolamine lauryl sulfonate |  |  |  |  |  |  |  |  |  |  |  |  |  |  |  |  |
| Triethanolamine polyoxyethylene lauryl sulfonate |  |  |  |  |  |  |  |  |  |  |  |  |  |  |  |  |
| Sodium α-Olefin sulfonate (C12) |  |  |  |  |  |  |  |  |  |  |  |  |  |  |  |  |
| Bubble volume | O | ⊙ | ⊙ | ⊙ | ⊙ | ⊙ | ⊙ | ⊙ | ⊙ | ⊙ | ⊙ | ⊙ | O | ⊙ | ⊙ | ⊙ |
| Retention of bubbles | O | O | O | O | O | O | O | O | O | O | O | O | O | O | O | O |
| Creaminess of bubbles | ⊙ | ⊙ | ⊙ | ⊙ | ⊙ | ⊙ | ⊙ | ⊙ | ⊙ | ⊙ | ⊙ | ⊙ | ⊙ | ⊙ | ⊙ | ⊙ |
| Touch of bubbles | O | O | O | ⊙ | O | O | O | ⊙ | O | O | O | ⊙ | O | O | O | ⊙ |
| Jarring feeling (hands) | Δ | Δ | O | O | Δ | Δ | O | O | Δ | Δ | O | O | O | Δ | O | O |
| Jarring feeling (hair) | Δ | Δ | O | O | Δ | Δ | O | O | Δ | Δ | O | O | Δ | Δ | O | O |
| Refreshed feeling | O | ⊙ | O | ⊙ | O | ⊙ | O | ⊙ | O | ⊙ | O | ⊙ | O | O | O | ⊙ |
| Total evaluation | 4 | 4 | 4 | 5 | 4 | 4 | 4 | 5 | 4 | 4 | 4 | 5 | 4 | 4 | 4 | 5 |

|  | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|
| Triethanolamine N-lauroylthreonate |  |  |  |  | 10 | 10 | 80 | 35 |  |  |  |  |  |  |  |  |
| Potassium N-lauroylthreonate | 10 | 10 | 80 | 35 |  |  |  |  | 10 | 10 | 80 | 35 | 10 | 10 | 80 | 35 |
| Sodium laurate | 10 | 80 | 10 | 35 |  |  |  |  | 10 | 80 | 10 | 35 | 10 | 80 | 10 | 35 |
| Triethanolamine laurate |  |  |  |  | 10 | 80 | 10 | 35 |  |  |  |  |  |  |  |  |
| Triethanolamine N-cocoylglutamate |  |  |  |  |  |  |  |  |  |  |  |  |  |  |  |  |
| Triethanolamine N-lauroylsarconate |  |  |  |  |  |  |  |  |  |  |  |  |  |  |  |  |
| Sodium N-lauroyl-N-methyl-β-alanate |  |  |  |  |  |  |  |  |  |  |  |  |  |  |  |  |
| Sodium polyoxyethylene lauryl acetate |  |  |  |  |  |  |  |  |  |  |  |  |  |  |  |  |
| Sodium cocoylisethionate | 80 | 10 | 10 | 30 |  |  |  |  |  |  |  |  |  |  |  |  |
| Sodium lauroylmethytaurate |  |  |  |  | 80 | 10 | 10 | 30 |  |  |  |  |  |  |  |  |
| Disodium lauryl sulfosuccinate |  |  |  |  |  |  |  |  | 80 | 10 | 10 | 30 |  |  |  |  |
| Disodium lauryl polyoxyethylene sulfosuccinate |  |  |  |  |  |  |  |  |  |  |  |  | 80 | 10 | 10 | 30 |
| Triethanolamine lauryl sulfonate |  |  |  |  |  |  |  |  |  |  |  |  |  |  |  |  |
| Triethanolamine polyoxyethylene lauryl sulfonate |  |  |  |  |  |  |  |  |  |  |  |  |  |  |  |  |
| Sodium α-Olefin sulfonate (C12) |  |  |  |  |  |  |  |  |  |  |  |  |  |  |  |  |
| Bubble volume | O | ⊙ | ⊙ | ⊙ | O | ⊙ | ⊙ | ⊙ | O | ⊙ | ⊙ | ⊙ | O | ⊙ | ⊙ | ⊙ |
| Retention of bubbles | O | O | O | O | O | O | O | O | O | O | O | O | O | O | O | O |

-continued

|  | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|
| Creaminess of bubbles | ⊙ | ⊙ | ⊙ | ⊙ | ⊙ | ⊙ | ⊙ | ⊙ | ⊙ | ⊙ | ⊙ | ⊙ | ⊙ | ⊙ | ⊙ | ⊙ |
| Touch of bubbles | ○ | ○ | ○ | ⊙ | ⊙ | ○ | ⊙ | ⊙ | ○ | ○ | ○ | ○ | ○ | ○ | ○ | ⊙ |
| Jarring feeling (hands) | △ | △ | ○ | ○ | △ | △ | ○ | ○ | △ | △ | ○ | ○ | △ | △ | ○ | ○ |
| Jarring feeling (hair) | △ | △ | ○ | ○ | △ | △ | ○ | ○ | △ | △ | ○ | ○ | △ | △ | ○ | ○ |
| Refreshed feeling | ○ | ⊙ | ○ | ⊙ | ○ | ⊙ | ○ | ⊙ | ○ | ⊙ | ○ | ⊙ | ○ | ⊙ | ○ | ⊙ |
| Total evaluation | 4 | 4 | 4 | 5 | 4 | 4 | 5 | 5 | 4 | 4 | 4 | 5 | 4 | 4 | 4 | 5 |

|  | 39 | 40 | 41 | 42 | 43 | 44 | 45 | 46 | 47 | 48 | 49 | 50 |
|---|---|---|---|---|---|---|---|---|---|---|---|---|
| Triethanolamine N-lauroylthreonate | 10 | 10 | 80 | 35 | 10 | 10 | 80 | 35 |  |  |  |  |
| Potassium N-lauroylthreonate |  |  |  |  |  |  |  |  | 10 | 10 | 80 | 35 |
| Sodium laurate |  |  |  |  |  |  |  |  | 10 | 80 | 10 | 35 |
| Triethanolamine laurate | 10 | 80 | 10 | 35 | 10 | 80 | 10 | 35 |  |  |  |  |
| Triethanolamine N-cocoylglutamate |  |  |  |  |  |  |  |  |  |  |  |  |
| Triethanolamine N-lauroylsarconate |  |  |  |  |  |  |  |  |  |  |  |  |
| Sodium N-lauroyl-N-methyl-β-alanate |  |  |  |  |  |  |  |  |  |  |  |  |
| Sodium polyoxyethylene lauryl acetate |  |  |  |  |  |  |  |  |  |  |  |  |
| Sodium cocoylisethionate |  |  |  |  |  |  |  |  |  |  |  |  |
| Sodium lauroylmethytaurate |  |  |  |  |  |  |  |  |  |  |  |  |
| Disodium lauryl sulfosuccinate |  |  |  |  |  |  |  |  |  |  |  |  |
| Disodium lauryl polyoxyethylene sulfosuccinate |  |  |  |  |  |  |  |  |  |  |  |  |
| Triethanolamine lauryl sulfonate | 80 | 10 | 10 | 30 |  |  |  |  |  |  |  |  |
| Triethanolamine polyoxyethylene lauryl sulfonate |  |  |  |  | 80 | 10 | 10 | 30 |  |  |  |  |
| Sodium α-Olefin sulfonate (C12) |  |  |  |  |  |  |  |  | 80 | 10 | 10 | 30 |
| Bubble volume | ⊙ | ⊙ | ⊙ | ⊙ | ○ | ⊙ | ⊙ | ⊙ | ○ | ⊙ | ⊙ | ⊙ |
| Retention of bubbles | ○ | ○ | ○ | ○ | ○ | ○ | ○ | ○ | ○ | ○ | ○ | ○ |
| Creaminess of bubbles | ⊙ | ⊙ | ⊙ | ⊙ | ⊙ | ⊙ | ⊙ | ⊙ | ○ | ⊙ | ⊙ | ⊙ |
| Touch of bubbles | ⊙ | ⊙ | ○ | ⊙ | ○ | ○ | ○ | ⊙ | ○ | ○ | ○ | ⊙ |
| Jarring feeling (hands) | △ | △ | ○ | ○ | △ | △ | ○ | ○ | △ | △ | ○ | △ |
| Jarring feeling (hair) | △ | △ | ○ | ○ | △ | △ | ○ | ○ | △ | △ | ○ | △ |
| Refreshed feeling | ○ | ⊙ | ○ | ⊙ | ○ | ⊙ | ○ | ⊙ | ○ | ⊙ | ○ | ⊙ |
| Total evaluation | 4 | 4 | 4 | 5 | 4 | 4 | 4 | 5 | 4 | 4 | 4 | 5 |

|  | 16 | 17 | 18 | 51 | 52 | 53 | 54 | 55 | 56 | 57 | 58 | 59 |
|---|---|---|---|---|---|---|---|---|---|---|---|---|
| Triethanolamine N-lauroylthreonate | 98.5 | 98.5 | 98.5 | 85 | 55 | 13.5 | 85 | 55 | 13.5 | 85 | 55 | 13.5 |
| Triethanolamine laurate |  |  |  | 13.5 | 43.5 | 85 | 13.5 | 43.5 | 85 | 13.5 | 43.5 | 85 |
| Cetyl trimethyl ammonium chloride | 1.5 |  |  | 1.5 | 1.5 | 1.5 |  |  |  |  |  |  |
| Lauryl dimethyl benzyl ammonium chloride |  | 1.5 |  |  |  |  | 1.5 | 1.5 | 1.5 |  |  |  |
| PCA ethyl N-cocoylarginate |  |  | 1.5 |  |  |  |  |  |  | 1.5 | 1.5 | 1.5 |
| Bubble volume | ○ | ○ | ○ | ⊙ | ⊙ | ⊙ | ⊙ | ⊙ | ⊙ | ⊙ | ⊙ | ⊙ |
| Retention of bubbles | X | X | X | ○ | ○ | ○ | ○ | ○ | ○ | ○ | ○ | ○ |
| Creaminess of bubbles | X | X | X | ○ | ⊙ | ⊙ | ○ | ⊙ | ⊙ | ○ | ⊙ | ⊙ |
| Touch of bubbles | △ | △ | △ | ○ | ⊙ | ○ | ○ | ⊙ | ○ | ○ | ⊙ | ⊙ |
| Jarring feeling (hands) | ○ | ○ | ○ | ○ | ○ | △ | ○ | ○ | △ | ○ | ⊙ | ○ |
| Jarring feeling (hair) | ○ | ○ | ○ | ⊙ | ⊙ | ○ | ⊙ | ⊙ | ○ | ⊙ | ⊙ | ⊙ |
| Refreshed feeling | △ | △ | △ | ○ | ⊙ | ⊙ | ○ | ⊙ | ⊙ | ○ | ⊙ | ⊙ |
| Total evaluation | 2 | 2 | 2 | 4 | 5 | 4 | 4 | 5 | 4 | 4 | 5 | 5 |

|  | 19 | 20 | 21 | 60 | 61 | 62 | 63 | 64 | 65 | 66 | 67 |
|---|---|---|---|---|---|---|---|---|---|---|---|
| Triethanolamine N-lauroylthreonate | 70 |  |  | 10 | 10 | 80 | 35 |  |  |  |  |
| Potassium N-lauroylthreonate |  | 50 |  |  |  |  |  | 10 | 10 | 80 | 35 |
| Potassium laurate |  |  |  |  |  |  |  | 10 | 80 | 10 | 35 |
| Triethanolamine laurate |  |  |  | 10 | 80 | 10 | 35 |  |  |  |  |
| Alkyl polyglycoside |  |  | 100 | 80 | 10 | 10 | 30 |  |  |  |  |
| Diethanolamide laurate | 30 | 50 |  |  |  |  |  | 80 | 10 | 10 | 30 |
| Bubble volume | ○ | ○ | △ | ○ | ⊙ | ⊙ | ⊙ | △ | ⊙ | ⊙ | ⊙ |
| Retention of bubbles | △ | △ | △ | ○ | ○ | ○ | ○ | △ | ○ | ○ | ○ |
| Creaminess of bubbles | X | X | △ | ○ | ⊙ | ○ | ⊙ | ○ | ○ | ○ | ⊙ |
| Touch of bubbles | △ | △ | △ | ○ | ○ | ○ | ⊙ | ○ | ○ | ○ | ○ |
| Jarring feeling (hands) | ○ | ○ | ○ | ○ | △ | ○ | ○ | ⊙ | △ | ○ | ○ |
| Jarring feeling (hair) | ○ | ○ | ○ | ○ | △ | ○ | ○ | ⊙ | △ | ○ | ○ |
| Refreshed feeling | △ | △ | X | ○ | ⊙ | ○ | ⊙ | ○ | ⊙ | ○ | ⊙ |
| Total evaluation | 3 | 3 | 3 | 4 | 4 | 4 | 5 | 4 | 4 | 4 | 5 |

| | 22 | 23 | 24 | 68 | 69 | 70 | 71 | 72 | 73 | 74 | 75 | 76 | 77 | 78 | 79 |
|---|---|---|---|---|---|---|---|---|---|---|---|---|---|---|---|
| Triethanolamine N-lauroylthreonate | | | | | | | | 10 | 10 | 80 | 35 | | | | |
| Potassium N-lauroylthreonate | | | 20 | 10 | 10 | 80 | 35 | | | | | 10 | 10 | 80 | 35 |
| Potassium laurate | | | | 10 | 80 | 10 | 35 | | | | | 10 | 80 | 10 | 35 |
| Triethanolamine laurate | | | | | | | | 10 | 80 | 10 | 35 | | | | |
| Lauryl dimethylaminoacetic acid betaine | 100 | | | 80 | 10 | 10 | 30 | | | | | | | | |
| Lauryl dimethylamino-2-hydroxypropyl sulfobetaine | | 100 | | | | | | 80 | 10 | 10 | 30 | | | | |
| 2-Lauryl-N-carboxymethyl-N-hydroxyethylimidazolinium bataine | | | 80 | | | | | | | | | 80 | 10 | 10 | 30 |
| Bubble volume | Δ | Δ | Δ | ○ | ⊙ | ⊙ | ⊙ | ○ | ⊙ | ⊙ | ⊙ | ○ | ⊙ | ⊙ | ⊙ |
| Retention of bubbles | X | X | X | ○ | ○ | ○ | ○ | ○ | ○ | ○ | ○ | ○ | ○ | ○ | ○ |
| Creaminess of bubbles | X | X | X | ○ | ○ | ○ | ⊙ | ○ | ⊙ | ○ | ⊙ | ○ | ⊙ | ○ | ⊙ |
| Touch of bubbles | Δ | Δ | Δ | ○ | ○ | ⊙ | ⊙ | Δ | ○ | ○ | ⊙ | Δ | ○ | ○ | ⊙ |
| Jarring feeling (hands) | ○ | ○ | ○ | ⊙ | Δ | ○ | ○ | ⊙ | Δ | ○ | ○ | ⊙ | Δ | ⊙ | ⊙ |
| Jarring feeling (hair) | ○ | ○ | ○ | ⊙ | Δ | ○ | ○ | ⊙ | Δ | ○ | ⊙ | ⊙ | Δ | ⊙ | ⊙ |
| Refreshed feeling | X | X | Δ | ○ | ⊙ | ○ | ⊙ | ○ | ⊙ | ○ | ⊙ | ○ | ⊙ | ○ | ⊙ |
| Total evaluation | 2 | 2 | 2 | 4 | 4 | 4 | 5 | 4 | 4 | 4 | 5 | 4 | 4 | 5 | 5 |

(c) Examples 80–97

The components as shown in the following Tables 11–28 were mixed in the compounding ratio (by weight) given there and various detergent compositions were prepared by a conventional method. Those detergent compositions exhibited excellent foam volumes, foam maintenance and foam creaminess and had excellent feel on use as well.

TABLE 11

(Soap bar)

| Composition | Content (%) |
|---|---|
| Sodium N-lauroylthreonate | 70 |
| Soap base | 20 |
| Cetyl alcohol | 5 |
| Water | 5 |

TABLE 12

(Shampoo)

| Composition | Content (%) |
|---|---|
| Triethanolamine N-cocoylthreonate | 8 |
| Triethanolamine laurate | 1 |
| Sodium lauryl sulfonate | 3 |
| Coconut oil fatty acid diethanolamide | 3 |
| Coconut oil fatty acid amidepropylbetaine | 3 |
| Polyethyleneglycol distearate | 1.5 |
| Glycerol | 5 |
| Antiseptic | 0.1 |
| Perfume | 0.1 |
| Water | balance |

TABLE 13

(Cleansing cream)

| Composition | Content (%) |
|---|---|
| Sodium N-lauroylthreonate | 20 |
| Sodium laurate | 5 |
| Monosodium lauryl phosphate | 5 |
| lauric acid diethanolamide | 2 |
| Propylene glycol | 5 |
| Polyethylene sorbitane monolaurate | 5 |
| Antiseptic | 0.2 |
| Perfume | 0.2 |
| Water | balance |

TABLE 14

(Cleansing form)

| Composition | Content (%) |
|---|---|
| Potassium N-myristoylthreonate | 20 |
| Potassium myristorate | 4 |
| Glycerol | 10 |
| PEG 400 | 15 |
| Dipropylene glycol | 10 |
| Lauroyl methyl taurine | 5 |
| POE · POP block polymer | 5 |
| POE(15)oleyl alcohol | 3 |
| Lanolin derivative | 2 |
| Antiseptic | 0.1 |
| Perfume | 0.1 |
| Water | balance |

TABLE 15

(Shampoo)

| Composition | Content (%) |
|---|---|
| Triethanolamine N-cocoylthreonate | 10 |
| Triethanolamine laurate | 2 |
| Distearyl dimethyl ammonium chloride | 0.2 |
| PCA ethyl N-cocoylarginate | 0.2 |
| Sodium lauryl sulfonate | 6 |
| Coconut oil fatty acid diethanolamide | 1 |
| Glycerol | 5 |
| Antiseptic | 0.1 |
| Perfume | 0.1 |
| Water | balance |

TABLE 16

(Shampoo)

| Composition | Content (%) |
|---|---|
| Triethanolamine N-cocoylthreonate | 10 |
| Coconaut oil fatty acid triethanolamine salt | 2 |
| Lauric acid diethanolamide | 4 |
| Triethanolamine lauroyl sulfonate | 8 |
| 1,3-Butylen glycol | 3 |
| Cationized cellulose | 0.4 |
| Hydrolyzed collagen | 0.5 |
| Antiseptic | 0.1 |
| Perfume | 0.1 |
| Water | balance |

TABLE 17

(Shampoo)

| Composition | Content (%) |
|---|---|
| Potassium N-cocoylthreonate | 15 |
| Coconut oil fatty acid potassium salt | 3 |
| Sodium pyrrolidoncarboxylate (50% solution) | 2 |
| Dioctyldodecyl N-lauroylglutamate | 0.5 |
| Dimethyl diallyl ammonium chloride acrylamide copolymer (8% solution) | 4 |
| Hydroxypropyl cellulose | 1 |
| Antiseptic | 0.1 |
| Perfume | 0.1 |
| Water | balance |

TABLE 18

(Shampoo)

| Composition | Content (%) |
|---|---|
| Triethanolamine N-lauroylthreonate | 15 |
| Triethanolamine laurate | 3 |
| Coconut oil fatty acid diethanolamide | 3 |
| N-(N'-Lanokin fatty acid amide propyl)-N-ethyl-N,N-dimethyl ammonium ethylsulfate (67% solution) | 1 |
| POE(60)myristylene(1)tallow alkyl ether | 2.5 |
| POE(40)hydrogenated castor oil monopyrroglutamate | 5 |
| Butylene glycol | 3 |
| MARINE DEW PC-100* | 10 |
| Ethylene glycol distearate | 1.2 |
| Antiseptic | 0.1 |
| Perfume | 0.1 |
| Water | balance |

*; Partially deacetylated chitin

TABLE 19

(Shampoo)

| Composition | Content (%) |
|---|---|
| Triethanolamine N-cocoylthreonate | 12 |
| Coconut oil fatty acid triethanolamine salt | 2 |
| Coconut oil fatty acid diethanolamide | 3 |
| Cationized cellulose | 0.2 |
| POE(60)myristylene(1)tallow alkyl ether | 3 |
| ELDEW CL-301* | 1 |
| Butylene glycol | 2 |
| Antiseptic | 0.1 |
| Perfume | 0.1 |
| Water | balance |

*; Di(cholesteryl, behenyl, octyldodecy) N-lauroyl-L-glutamate

TABLE 20

(Shampoo)

| Composition | Content (%) |
|---|---|
| Triethanolamine N-lauroylthreonate | 6 |
| Sodium N-lauroylmethyltaurate | 3 |
| Triethanolamine laurate | 10 |
| Triethanolamine myristrate | 10 |
| Lauryl imidazolinium betaine | 5 |
| Lauryl diethanolamide | 5 |
| Propylene glycol | 7 |
| Lauryl dimethyl amine oxide | 2 |
| Antiseptic | 0.1 |
| Perfume | 0.1 |
| Water | balance |

TABLE 21

(Shampoo)

| Composition | Content (%) |
|---|---|
| Potassium N-cocoylthreonate | 8 |
| Potassium laurate | 1 |
| Coconut oil alkyl dimethyl aminobetaine | 10 |
| Coconut oil fatty acid diethanolamide | 5 |
| Sodium chloride | 2 |
| Mannitol | 20 |
| Methylparaben | 0.2 |
| Sodium benzoate | 0.2 |
| Sodium citrate | 0.5 |
| Water | balance |

TABLE 22

(Cleansing liquid)

| Composition | Content (%) |
|---|---|
| Sodium N-cocoylthreonate | 3 |
| Triethanolamine laurate | 10 |
| Sodium polyoxyethylene lauryl acetate | 5 |
| Lauryl hydroxy sulfobetaine | 2 |
| Hydroxyproline | 0.1 |
| Ethylene glycol distearate | 2 |
| D-glucose | 30 |
| Hydroxypropylcellulose | 2 |
| Aloe extract | 1 |
| Lithospermum root extract | 2 |
| Antiseptic | 0.1 |
| Perfume | 0.1 |
| Water | balance |

TABLE 23

(Shampoo)

| Composition | Content (%) |
|---|---|
| Potassium N-lauroylthreonate | 5 |
| Potassium laurate | 1 |
| Sodium N-lauroyl-methyl-β-alanate | 5 |
| Sodium lauryl sulfate | 2 |
| Lauroyl diethanolamide | 3 |
| Carboxyvinyl polymer | 2 |
| Hydrolyzed collagen | 1 |
| Sodium pyrroridoncarboxylate (50% solution) | 5 |
| Citric acid | 1 |
| Squalene | 0.5 |
| 2-Phenoxyethanol | 0.1 |
| Methylparaben | 0.2 |
| Perfume | 0.2 |
| Water | balance |

TABLE 24

(Shampoo)

| Composition | Content (%) |
|---|---|
| Potassium N-myristoylthreonate | 10 |
| Potassimu myristyrate | 5 |
| Coconut oil alkyl dimethylaminobetaine | 5 |
| Coconut oil fatty acid potassium salt | 5 |
| Glycol | 3 |
| Hydroxymethylcellulose | 2 |
| EDTA | 0.1 |
| Methylparaben | 0.2 |
| Perfume | 0.1 |
| Water | balance |

TABLE 25

(Acidic shampoo)

| Composition | Content (%) |
| --- | --- |
| Potassium N-cocoylthreonate | 15 |
| Coconut oil fatty acid potassium salt | 2 |
| Potassium myristyrate | 2 |
| Glycerol | 3 |
| Lauroyl diethanolamide | 5 |
| Sorbitol | 4 |
| Citric acid | 2 |
| Methylparaben | 0.1 |
| Perfume | 0.1 |
| Water | balance |

TABLE 26

(Cleansing foam)

| Composition | Content (%) |
| --- | --- |
| Sodium N-lauroylthreonate | 25 |
| Sodium laurate | 5 |
| Glycerol | 20 |
| PEG 400 | 10 |
| 1,3-Butylene glycol | 10 |
| Methylparaben | 0.2 |
| Perfume | 0.3 |
| Water | balance |

TABLE 27

(Shampoo)

| Composition | Content (%) |
| --- | --- |
| Triethanolamine N-lauroylthreonate | 25 |
| Triethanolamine laurate | 6 |
| Dipotassium glycyrrhizinate | 0.2 |
| Allantoin | 0.4 |
| Dibutyl hydroxytoluene | 0.2 |
| Ethanol | 3 |
| Perfume | 0.5 |
| Water | balance |

TABLE 28

(Cleansing)

| Composition | Content (%) |
| --- | --- |
| Triethanolamine N-lauroylthreonate | 25 |
| Triethanolamine laurate | 6 |
| Polyoxypropylene(11)polyoxyethylene(4) butylether (HLB 7.2) | 5 |
| Dibutyl hydroxytoluene | 0.2 |
| Ethanol | 3 |
| Perfume | 0.3 |
| Water | balance |

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A detergent composition comprising (A) an N-acylthreonine salt in which the acyl group is a fatty acid residue having 8–22 carbon atoms and (B) a higher fatty acid salt having 8–22 carbon atoms.

2. The detergent composition according to claim 1, wherein said composition further comprises at least one anionic surface-active agent of a carboxylate type (excluding components (A) and (B)), a sulfonate type or a sulfate type.

3. The detergent composition according to claim 1, wherein said composition further comprises at least one cationic surface-active agent of an aliphatic amine quaternary ammonium salt type, an aromatic quaternary ammonium salt type or a mono(long-chain acyl) basic amino acid lower alkyl ester type.

4. The detergent composition according to claim 1, wherein said composition further comprises at least one nonionic surface-active agent of an alkyl glycoside type or an aliphatic alkanolamide type.

5. The detergent composition according to claim 1, wherein said composition further comprises at least one amphoteric surface-active agent of a betaine type or an imidazoline type.

6. The composition according to claim 1, wherein the ratio of components (A) to (B) are within a range from 0.5:99.5 to 99.5:0.5 by weight, based on the total weight of the composition.

7. The composition of claim 1, wherein said fatty acid is lauric acid, myristic acid, palmitic acid, stearic acid, oleic acid, coconut oil fatty acids, tallow fatty acids, hydrogenated tallow fatty acids, castor oil fatty acids, olive oil fatty acids or palm oil fatty acids.

8. The composition of claim 1, wherein said N-acylthreonine salt is N-lauroylthreonine, N-myristoylthreonine, N-palmitoylthreonine, N-stearoylthreonine, N-oleoylthreonine, N-cocoylthreonine or an acylthreonine derived from N-hydrogenated tallow fatty acids.

9. The composition of claim 1, wherein the salt components of said N-acylthreonine salt and said higher fatty acid salt are, independently, an alkali metal; an alkali earth metal; an organic amine; a basic amino acid; ammonia or a mixture thereof.

10. The composition of claim 3, wherein said cationic surfactant is a linear mono or dialkyl quaternary ammonium salt is of the formula (3):

where one or two of $R^4$–$R^7$ are long-chain alkyl having 8–24 carbon atoms while others are alkyl or hydroxyalkyl having 1–3 carbon atoms; and X is a halogen atom or an alkyl sulfate group having 1 or 2 carbon atoms.

11. The composition of claim 3, wherein said aromatic quaternary ammonium salt is a benzalconium salt of the formula (4):

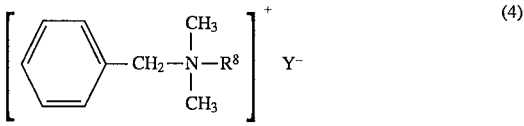

wherein $R^8$ is an alkyl having 8–24 carbon atoms; and

Y is a halogen atom or an alkyl sulfate group having 1 or 2 carbon atoms.

12. The composition of claim 11, wherein said benzalconium salt is lauryl dimethylbenzylammonium chloride, stearyl dimethylbenzylammonium chloride or a mixture thereof.

13. The composition of claim 3, wherein the acyl group of said mono(long-chain acyl) basic amino acid lower alkyl ester salt is an acyl residuce of a fatty acid having 8–22 carbon atoms.

14. The composition of claim 13, wherein said acyl group is lauroyl, cocoyl, myristoyl, palmitoyl, stearoyl or oleyl.

15. The composition of claim 3, wherein the the basic amino acid of said mono(long-chain acyl) basic amino acid lower alkyl ester salt is lysine, ornithine or arginine.

16. The composition of claim 3, wherein the the salt of said mono(long-chain acyl) basic amino acid lower alkyl ester salt is an inorganic salt or an organic salt.

17. The composition of claim 16, wherein said inorganic salt is hydrochloride or sulfate.

18. The composition of claim 16, wherein said organic salt is acetate, tartrate, citrate, p-toluenesulfonate, fatty acid salts, acidic amino acid salts or pyroglutamate.

19. The composition of claim 3, wherein the the lower alkyl ester component of said mono(long-chain acyl) basic amino acid lower alkyl ester salt is methyl ester, ethyl ester, propyl ester, butyl ester, pentyl ester, hexyl ester, heptyl ester or octyl ester.

20. The composition of claim 5, wherein said amphoteric surface-active agent is a betaine type, a carbobetaine type, an amidobetaine type, a sulfobetaine type, a hydroxysulfobetaine type, an amidosulfobetaine type, a phosphobetaine type or a imidazoline type.

21. The composition of claim 20, wherein said amphoteric surface-active agent is coconut oil alkyldimethylaminoacetic acid betaine, coconut oil fatty acid amide propyldimethylaminoacetic acid betaine, stearyl dihydroxyethylaminoacetic acid betaine, lauryl hydroxysulfobetaine, lauryl sulfobetaine or lauryl phosphobetaine.

* * * * *

UNITED STATES PATENT AND TRADEMARK OFFICE
CERTIFICATE OF CORRECTION

PATENT NO. : 5,616,552
DATED: : APRIL 1, 1997
INVENTOR(S) : HIDEKI YOSHIHARA ET AL

It is certified that error appears in the above-identified patent and that said Letters patent is hereby corrected as shown below:

Column 9, line 62, "creay" should read --creamy--.

Column 11, Table 2, line 11, "Sfflium" should read --Sodium--.

Column 16, line 58, "Coconaut" should read --Coconut--.

Column 17, line 50, "octyldodecy" should read --octyldodecyl--.

Column 21, line 1, "residuce" should read --residue--.

Signed and Sealed this

Fourteenth Day of July, 1998

Attest:

BRUCE LEHMAN

Attesting Officer

Commissioner of Patents and Trademarks